United States Patent [19]

Kervennal et al.

[11] 4,332,739

[45] Jun. 1, 1982

[54] PROCESS FOR THE MANUFACTURE OF AROMATIC ISOCYANATES

[75] Inventors: Jacques Kervennal, Lyons; Boubaker Elleuch, Rilleux-la-Pape; Younès B. Taarit, Lyons, all of France

[73] Assignee: Produits Chimiques Ugine Kuhlmann, Courbevoie, France

[21] Appl. No.: 203,249

[22] Filed: Nov. 3, 1980

[30] Foreign Application Priority Data

Nov. 27, 1979 [FR] France .................................. 79 29123

[51] Int. Cl.$^3$ .......................................... C07C 118/06
[52] U.S. Cl. .............................................. 260/453 PC
[58] Field of Search .................................. 260/453 PC

[56] References Cited

U.S. PATENT DOCUMENTS 3,523,966  8/1970  Ottmann et al. ............. 260/453 PC
3,828,089  8/1974  Hammond et al. .......... 260/453 PC

*Primary Examiner*—Dolph H. Torrence
*Attorney, Agent, or Firm*—Sigalos & Levine

[57] ABSTRACT

Process for the manufacture in the liquid phase of aromatic isocyanates by the reaction of aromatic nitro compounds with carbon monoxide in the presence of a catalyst comprising a zeolite containing at least one active metal selected from Group VIII or $I_B$ of the Periodic Table of the Elements in the form of a cation or of a metallic crystallite in the zeolite.

13 Claims, No Drawings

PROCESS FOR THE MANUFACTURE OF AROMATIC ISOCYANATES

BACKGROUND OF THE INVENTION

The present invention concerns a process for the manufacture of organic isocyanates from nitro compounds and, more particularly, a process for the preparation of aromatic isocyanates by the reaction between aromatic nitro compounds and carbon monoxide.

Aromatic isocyanates are organic intermediates of great interest. Two among them are particularly well known, namely, toluene diisocyanate and diphenylmethane-4,4'-diisocyanate which are used in the synthesis of polyurethanes. The industrial processes for the preparation of these products all involve the phosgenation reaction of an amine coming from the catalytic hydrogenation of a nitro derivative. The disadvantages of these processes are many. Specifically, they require the synthesis and manipulation of phosgene, a very dangerous product, and they produce hydrochloric acid in large quantities and therefore require the erection and costly maintenance of a special installation for the electrolysis of this acid in order to recycle the chlorine.

The advantage presented by a process avoiding the use of phosgene is obvious. Catalytic compositions permitting the preparation of isocyanates by the reaction of an organic nitro compound with carbon monoxide, at high temperature and pressure, are described in several patents. It is thus that the use, as catalyst, of a noble halide in the presence of a basic aromatic amine is described in French Pat. No. 1,600,529. Catalysts formed of halides or oxides of Ru, Rh, Pd, Os, Ir, Pt and of a heteroaromatic sulfur-containing compound in the presence possibly of an oxide of Cr, Mo, Nb, W, and V are described in West German Pat. No. 1,910,303. The use of a catalytic system formed of a noble metal halide and of an organic phosphorous compound, for instance a triaryl phosphine or a phosphite, is described in French Pat. No. 1,567,321. Catalytic systems composed of one or several palladium and/or rhodium halides, one or several heteroatomic nitrogenous bases and of a co-catalyst formed of one or several iron borates are described in French Pat. No. 2,155,242. In French Pat. No. 2,120,110 besides a palladium halide and heterocyclic nitrogenous bases, the catalytic formulation includes a co-catalyst composed of one or several iron and/or manganese molybdates. Certain attempts have been made to deposit the active phases on supports; it is thus that French Pat. No. 1,600,529 and No. 1,558,896, as well as U.S. Pat. No. 3,728,370 envision, without practical illustration, the deposition of the catalyst on supports of the type of alumina, silica, carbon, barium sulfate, calcium carbonate, asbestos, bentonite, diatomaceous earth, and Fuller's earth. The use of palladium, palladium chloride or rhodium chloride on alumina, silica and silicon carbide for the carbonylation, in the vapor phase, of nitro derivatives is described in British Pat. No. 1,257,932, and a publication by W. B. Hardy and R. P. Bennett in Tetrahedron Letters No. 11, p. 961 (1967) gives the results obtained with a catalyst consisting of rhodium on carbon, to which $FeCl_3$ had been added, in the carbonylation of nitrobenzene to form phenyl isocyanate.

All of these systems based on precious metals make it possible to produce isocyanates from nitro compounds with variable selectivities and productivities. However, their difficult and costly recovery prevents commercial industrial use.

SUMMARY OF THE INVENTION

The present invention permits the direct reduction reaction of aromatic nitro compounds with carbon monoxide to form isocyanates with good yields in a simple and commercially feasible manner.

The present invention is directed to a process for the manufacture of aromatic isocyanates comprising reacting an aromatic nitro compounds with carbon monoxide in the presence of a catalyst comprising a zeolite containing at least one introduced active metal.

DETAILED DESCRIPTION

In carrying out the process of the instant invention, the nitro compounds are placed in contact with carbon monoxide at elevated temperature and pressure, in the presence of one or more zeolites containing at least one active metal. It is possible to operate in the presence of an organic solvent, by batch technique in an equipment set-up of the autoclave type or by a continuous technique which makes it possible to eliminate the isocyanate produced as soon as it is formed. The equation for the reaction can be written according to the following scheme:

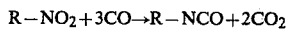

$$R-NO_2 + 3CO \rightarrow R-NCO + 2CO_2$$

The process according to the invention is applicable to aromatic compounds including one or several nitro groups attached to a carbon atom of an aromatic ring. These compounds, known as base materials for the preparation of aromatic mono- and diisocyanates, can be represented by the formula:

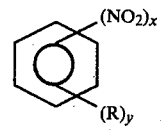

in which $x = 1$ or 2, and $y = 0, 1, 2,$ or 3, with R represent an alkyl group having from 1 to 10 carbon atoms, a halogen atom, chlorine or bromine for instance, or an alkoxy group $OR'$ in which $R'$ is an alkyl radical having from 1 to 10 carbon atoms. Non-limiting examples of aromatic compounds having one or more nitro groups and which can be used according to the invention are nitrobenzene, ortho-nitrotoluene, para-nitrotoluene, 1,2-dinitrobenzene, 1,3-dinitrobenzene, 1,4-dinitrobenzene, 2,4-dinitrotoluene, 2,6-dinitrotoluene, 1-methoxy-2,4-dinitrobenzene, 1-chloro-2-nitrobenzene, or 1-chloro-2,4-dinitrobenzene.

The process according to the invention is likewise applicable to aromatic nitro compounds possessing several rings substituted by one or several nitro functions such as, for instance, in non-limiting manner, 2,4'-dinitrostilbene, 4,4'-dinitrostilbene, 2,4'-dinitrodibenzyl, 4,4'-dinitrodibenzyl.

Picking up the definition given by J. V. Smith in Amer. Mineral Soc. Spec. paper, 1,281 (1963), zeolites are aluminosilicates whose structure comprises cavities occupied by ions whose great freedom of movement more particularly allows ion exchanges. This makes possible the introduction of metals by standard ion exchange techniques, with the metallic cation then keeping an environment very close to the one which it has in organometallic complexes and the access of reactants remaining very easy. Impregnation by salts or metallic complexes is likewise possible. According to the present invention, such zeolites containing introduced metallic cations or metals are particularly suitable for catalyzing the direct carbonylation of aromatic nitro derivatives to form isocyanates. Among the zeolites in conformity with the invention there are to be found, in non-limiting manner, cancrinite, chabazite, zeolite A, erionite, faujasite Y, gmelinite, zeolite L, mazzite, mordenite, and sodalite.

The following general operating manner can be used in order to introduce a metallic cation into the zeolite. The required quantity of metallic salt, for instance a metal halide, is dissolved in an excess of ammonium hydroxide by heating under refluxing. The excess ammonium hydroxide (ammonia) is eliminated by evaporation of the solution containing the aminohalide having been formed, then water is added to the solution and the cationic exchange is carried out by placing the zeolite in contact with the aqueous solution of the metal ion complex under agitation at ambient temperature. The end of the exchange is indicated when the solution becomes colorless.

The zeolite containing the metallic cation thus having been introduced can be used as is as catalyst for the direct carbonylation reaction of aromatic nitro derivatives resulting in the formation of isocyanates. However, it can be advantageous to have it undergo an activation treatment under oxygen between 100° C. and 600° C., which can possibly be followed by a reducing treatment under hydrogen between 50° C. and 600° C. for the purpose of reducing the metallic cation into metal.

The metals which are particularly suitable for the invention are the metals of Groups VIII and $I_B$ of the Periodic Table of the Elements and particularly: iron, cobalt, nickel, ruthenium, rhodium, palladium, iridium, copper and silver.

The metals can be introduced into the zeolites in different forms such as salts or complexes, but preferably in the form of halides such as chloride or bromide. The metal content in the zeolite can vary between 0.1 and 30% of the weight of the overall catalyst, preferably between 1 and 15% by weight.

The concentration of the catalyst in the reaction medium, expressed by the ratio of the number of gram atoms of the metal to the number of nitro groups to be converted, can vary between $10^{-4}$ and 1 and preferentially between $5 \times 10^{-3}$ and $10^{-1}$.

The reaction can be carried out in the absence of solvent, but the presence of a solvent generally promotes selective formation of isocyanate. The solvents preferentially used are saturated or aromatic hydrocarbons such as hexane, heptane, n-decane, Decalin (decahydronaphthalene), benzene, toluene or xylene, and aromatic halides such as chlorobenzene and the dichlorobenzenes; solvents containing fluorine, such as perfluoromethylDecalin and trichlorotrifluoroethane, can likewise be used.

On operating in the presence of a solvent, the proportion is not critical, but one operates in general with solutions containing from 5 to 50% by weight of the nitro compound in the solvent. It is recommended to add to the reaction medium quantities of pyridine going from 0.1 to 30 moles per mole of nitro compound and, preferentially, from 0.5 to 10 moles per mole of nitro compound, for the purpose of improving the isocyanate selectivity.

The reaction temperatures are between 100° C. and 500° C. and, more particularly, between 150° C. and 300° C., depending on the nature and the stability of the reactants involved under operating conditions.

The reaction pressures are between 20 and 500 bars, preferably between 150 and 350 bars, and must be sufficient in order to keep a large fraction of the reactants in the liquid phase and to introduce a total quantity of carbon monoxide corresponding to a molar ratio of ($CO/NO_2$ group) generally between 3 and 100 and, preferably, between 10 and 65.

The process according to the invention is particularly advantageous for the manufacture of toluene diisocyanate and of phenyl isocyanate which, when carbamated with a low-molecular-weight alcohol such as methanol or ethanol, can serve as the base material in the manufacture of diphenylmethane-4,4'-diisocyanate according to the description published in Chemical Week, p. 57, of Nov. 9, 1977.

The invention will be further described in connection with the examples that follow which are set forth for purposes of illustration only. The trials described in the examples below are carried out in a batch manner in a stainless steel autoclave equipped with a magnetic agitator, capable of operating under pressures up to 500 bars and temperatures of 300° C. The autoclave, having been charged with the different reactants, and in some cases a solvent, and the catalyst, is then flushed with nitrogen before being placed under carbon monoxide pressure at ambient temperature. The autoclave is then heated to the selected temperature and the progress of the reaction is monitored by recording of the pressure. After the reaction, the isocyanate content values are evaluated by chemical determination with dibutyl amine, and the content values of residual nitro derivatives and possibly of azo derivatives were determined by gas liquid chromatography.

After the reaction, the zeolite containing the metal is easily recoverable by filtration; it can be recycled as is or it can undergo a regeneration treatment before reuse.

The results shown in the examples are expressed in terms based on the following definitions:

O.D.C., (overall degree of conversion) =

$$\frac{\text{number of moles of nitro derivative converted}}{\text{number of moles of nitro derivative introduced}} \times 100$$

Isocyanate selectivity =

$$\frac{\text{number of moles of isocyanate formed}}{\text{number of moles of nitro derivative converted}} \times 100$$

Isocyanate yield =

$$\frac{\text{number of moles of isocyanate formed}}{\text{number of moles of nitro derivatives introduced}} \times 100$$

EXAMPLE 1

A sample of zeolite containing palladium is prepared according to the description made by C. Naccache, J. F. Dutel and M. Che in J. Catalysis (1973), 29, 179. 3.3 g of thus formed palladium chloride are treated under refluxing with an excess of a solution of concentrated ammonium hydroxide. After total dissolution, the ammonia is evaporated until the pH of the solution is neutral. The solution is then divided into three equal parts.

The first third of the solution is placed in contact with 20 g of zeolite of the faujasite Y type and stirred for 8 hours at 80° C. After filtration and repeated washing with distilled water, the zeolite is placed in contact in the same manner with the second third of the solution of palladium tetraamminochloride. The operation is repeated with the last portion of of the solution. After drying, 22 g of zeolite containing about 10% of palladium are obtained.

2 g of the zeolite, ion exchanged and dried at 80° C., are treated in a glass chamber under a stream of oxygen of 1.2 liters/hour introduced through a fritted surface. Heating at a slow linear temperature rise at a rate of 0.5° C./min is maintained up to 350° C., following which the sample is conditioned in vacuo. The solid obtained then essentially contains bivalent palladium.

EXAMPLE 2

1 g of the final sample obtained in Example 1 is reduced under a stream of hydrogen at 200° C. The zeolite obtained then contains homodispersed metallic palladium.

EXAMPLE 3

An autoclave with a capacity of 300 ml is charged with 6 g of nitro-benzene, 0.6 g of zeolite catalyst prepared according to Example 1, and the total volume is filled up to 80 ml with ortho-dichlorobenzene. The reactor is closed and after flushing with nitrogen, 200 bars of carbon monoxide are introduced, and then the temperature is raised to 240° C. The reaction is allowed to take place for 6 hours, while maintaining stirring, and then the mixture is cooled and analyzed. The overall degree of conversion of the nitrobenzene is 95.5% and the phenylisocyanate selectivity is 35%.

The used catalyst is recovered by filtration and recycled without prior treatment in an autoclave of 300 ml capacity with 6 g of nitrobenzene. The total volume is filled up to 80 ml with ortho-dichlorobenzene and the operation is carried out as previously. At the end of 8 hours of reaction, the autoclave is cooled and analyses indicate that the overall degree of conversion of the nitrobenzene is 76% and the phenylisocyanate selectivity is 20%.

EXAMPLE 4

8 g of nitrobenzene and 0.8 g of zeolite catalyst prepared in Example 2 are placed into an autoclave of 300 ml capacity and the total volume is filled up to 80 ml with ortho-dichlorobenzene. The operation is carried out as in Example 3 by allowing the reaction to take place for 6 hours. The overall degree of conversion of the nitrobenzene is 87% and the phenylisocyanate selectivity is 33%.

EXAMPLE 5

A zeolite of the faujasite Y type containing 10% of palladium is prepared under the conditions of Example 1 and subjected to baking under oxygen, with a linear temperature programming of 0.5° C. per minute up to 500° C. 0.6 g of this is placed into an autoclave of 300 ml capacity with 6 g of nitrobenzene and the total volume is filled up to 80 ml with ortho-dichlorobenzene. The operation is carried out as in Example 3, with a reaction time of 6½ hours. After cooling, analysis indicates an overall degree of conversion of the nitrobenzene of 95.5% and a phenylisocyanate selectivity of 56%.

EXAMPLE 6

0.7 g of the palladium-containing zeolite prepared for Example 5, 10 g of nitrobenzene, and 0.2 g of pyridine are placed into an autoclave of 500 ml capacity and the total volume is filled up to 100 ml with ortho-dichlorobenzene. The operation is carried out as in Example 3 by allowing the reaction to proceed for 7½ hours. After cooling, analysis indicates an overall degree of conversion of the nitrobenzene of 100% and a phenylisocyanate selectivity of 77%.

EXAMPLE 7

A sample of the zeolite containing $Pd^{2+}$ ions and baked under oxygen as prepared in Example 5 is taken and subjected to a reducing treatment under hydrogen at 500° C. identical to the treatment described in Example 2. 1 g of this catalyst is then placed into an autoclave of 500 ml capacity, as well as 10 g of nitrobenzene and 0.2 g of pyridine, and the total volume is filled up to 100 ml with ortho-dichlorobenzene. The operation is carried out as in Example 3, with a reaction time of 6 hours. After cooling, analysis indicates an overall degree of conversion of the nitrobenzene of 100% and a phenylisocyanate selectivity of 78%.

The used catalyst is recovered by filtration and placed into a pyrex baking tube, through which a stream of oxygen is made to pass at the rate of 4 liters per hour and the temperature is raised linearly at a rate of 0.5° C./min up to 500° C. A stream of hydrogen is then made to pass at the same temperature.

0.4 g of the catalyst having been treated thus are then introduced into an autoclave of 500 ml capacity, together with 6 g of nitrobenzene and 0.2 g of pyridine, and the volume is filled up to 100 ml with ortho-dichlorobenzene. The operation is carried out as in Example 3, with a reaction time of 4 hours. After cooling, analysis indicates an overall degree of conversion of the nitrobenzene of 100% and a phenylisocyanate selectivity of 75%.

EXAMPLE 8

0.7 g of palladium-containing zeolite prepared according to the initial operating method of Example 7 are placed into an autoclave of 500 ml capacity. 20 g of nitrobenzene and 0.2 g of pyridine are added and the volume is filled up to 100 ml with ortho-dichlorobenzene. After 5½ hours of reaction under conditions analogous to those of Example 3, the mixture is analyzed. The overall degree of conversion of the nitrobenzene amounts to 100% and the phenylisocyanate selectivity amounts to 67.5%.

EXAMPLE 9

0.7 g of a palladium-containing zeolite prepared according to the initial operating method of Example 7 are introduced into an autoclave of 500 ml capacity. 120 g of nitrobenzene and 0.2 g of pyridine are added. After 5 hours of reaction under conditions identical to those of Example 3, the mixture is analyzed. 23 g of nitrobenzene have been converted (overall degree of conversion: 19.5%) and 8 g of phenylisocyanate have been formed (selectivity: 35%).

EXAMPLE 10

An autoclave of 500 ml capacity is charged with 0.8 g of a palladium-containing zeolite prepared according to the initial operating method of Example 7. 7.5 g of 2,4-dinitrotoluene and 0.2 g of pyridine are added, and the total volume is filled up to 100 ml with ortho-dichlorobenzene. The operation is carried out as in Example 3, with a reaction time of 4 hours. After cooling, analysis indicates an overall degree of conversion of the dinitrotoluene of 78%, with a toluene-2,4-diisocyanate selectivity of 7% and a selectivity in monoisocyanates of 63.5%.

EXAMPLE 11

A sample of zeolite containing rhodium is prepared according to the technique described in Example 1, from rhodium trichloride and zeolite of the faujasite Y type. After drying, zeolite containing 5.5% of rhodium is recovered and subjected to baking under oxygen with a linear temperature programming of 0.5° C. per minute up to 500° C., followed by a reducing treatment under hydrogen at 500° C. 1 g of the rhodium-containing zeolite having been thus prepared and treated, 0.2 g of pyridine and 10 g of nitrobenzene are introduced into an autoclave of 500 ml capacity, and the total volume is filled up to 100 ml with ortho-dichlorobenzene. The operation is carried out as in Example 3, with a reaction time of 7 hours. The overall degree of conversion of the nitrobenzene amounts to 80% and the phenylisocyanate selectivity amounts to 60%.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. The process for the manufacture of aromatic isocyanates comprising reacting, in the liquid phase, an aromatic nitro compound with carbon monoxide in the presence of a catalyst comprising a zeolite containing at least one introduced active metal.

2. The process of claim 1, wherein the active metal is in the form of a cation or a metal crystallite.

3. The process of claim 1 or 2 wherein the active metal is selected from a metal of Group VIII or Group $I_B$ of the Periodic Table of the Elements.

4. The process of claim 1 or 2 wherein the metal is palladium.

5. The process of claim 1 or 2 wherein the concentration by weight of the metal in the zeolite is between 0.1 and 30% of the weight of the overall catalyst.

6. The process of claims 1 or 2 wherein the ratio of the number of gram atoms of the metal to the number of nitro groups to be converted is between $10^{-4}$ and 1.

7. The process of claims 1 or 2 wherein the action of the catalyst takes place in the presence of a solvent in the reaction medium.

8. The process of claims 1 or 2 wherein the action of the catalyst takes place in the presence of a solvent and pyridine.

9. The process of claims 1 or 2 wherein the action takes place in the presence of a solvent and pyridine present in an amount between 0.1 and 30 moles per mole of nitro compound to be converted.

10. The process of claims 1 or 2 wherein the reaction medium is kept at a temperature between 100° C. and 500° C.

11. The process of claims 1 or 2 wherein the reaction medium is kept under a pressure of 20 to 500 bars.

12. The process of claim 1 wherein the aromatic isocyanate is a mono- or diisocyanate; the catalyst consists essentially of a zeolite containing at least one introduced active metal in the form of a cation or crystallite selected from a metal of Group VIII or Group IB of the Periodic Table of the Elements and present in an amount of 0.1 to 30% of the total weight of the catalyst; and the reaction takes place in the presence of a solvent and pyridine at a temperature between 100° C. and 500° C. and a pressure of 20 to 500 bars.

13. The process of claim 1 wherein the active metal is palladium, the solvent is a saturated or aromatic hydrocarbon, pyridine is present in an amount of 0.5 to 10 moles per mole of nitro compound, the reaction temperature is between 150° C. and 300° C., and the reaction pressure is between 150 and 350 bars.

* * * * *